(12) United States Patent
Komiyama

(10) Patent No.: US 6,206,692 B1
(45) Date of Patent: Mar. 27, 2001

(54) DENTAL IMPRESSION STOCK TRAY

(75) Inventor: Tomonobu Komiyama, Urawa (JP)

(73) Assignee: Hideko Komiyama, Saitama (JP)

( * ) Notice: Subject to any disclaimer, the term of this patent is extended or adjusted under 35 U.S.C. 154(b) by 0 days.

(21) Appl. No.: 09/547,477

(22) Filed: Apr. 12, 2000

(30) Foreign Application Priority Data

Apr. 13, 1999 (JP) ................................................. 11-105260

(51) Int. Cl.⁷ .................................................... A61C 9/00
(52) U.S. Cl. ................................................. 433/37; 433/41
(58) Field of Search ................... 433/37, 41, 47, 433/45

(56) References Cited

U.S. PATENT DOCUMENTS

| | | | | |
|---|---|---|---|---|
| 2,470,679 | * | 5/1949 | Beers | 433/37 |
| 3,878,610 | * | 4/1975 | Coscina | 433/37 |
| 3,978,585 | * | 9/1976 | Holcomb | 433/41 |
| 4,227,877 | * | 10/1980 | Tureaud et al. | 433/37 |
| 5,190,457 | * | 3/1993 | Schreinemakers | 433/37 X |

* cited by examiner

*Primary Examiner*—Nicholas D. Lucchesi
(74) *Attorney, Agent, or Firm*—Allen, Dyer, Doppelt, Milbrath & Gilchrist, P.A.

(57) ABSTRACT

Improved dental stock trays capable of taking a precise impression without an individual tray are disclosed. The improved trays are made by newly adding several features to conventional stock trays. For a dentulous maxilla, the improved maxillary tray comprises the added features: a small through hole at the front and central position in a side wall, a projecting plate at the convex and central position in a base, projections at the rear edge positions in the base, and protuberances at the rear end positions in an outer surface of the side wall. The hole, plate, projections and protuberances are in the neighborhoods facing an incisive papilla (or a median frenum), a median palatine raphe (or a palatine foveola), a hamular notch and a maxillary tuberosity, respectively, when the tray is inserted in a mouth.

8 Claims, 19 Drawing Sheets

DENTAL IMPRESSION STOCK TRAY

BACKGROUND OF THE INVENTION

The present invention relates to improved dental stock trays for taking an impression of a dentulous or edentulous mouth, particularly to the ones used for the following purposes: in general dental treatment, manufacturing a complete denture, a partial plate denture, a crown restoration or a treatment apparatus for a periodontal disease; in pediatric dentistry, manufacturing a complete denture, a partial plate denture or a crown restoration; in orthodontics, manufacturing an orthodontic appliance; manufacturing an apparatus for surgically treating a mouth including a temporomandibular joint; manufacturing a mouthpiece used in hard sports, such as boxing, karate, judo, soccer, football and baseball; during research in legal medicine or criminal investigation, collecting data or evidence thereof; manufacturing a mouthpiece used in eating or drinking and removed thereafter for deodorization or prevention of tooth decay; manufacturing a mouthpiece used in singing, playing a wind instrument or practicing pronunciation; or treating teeth of an animal.

Moreover, the present invention relates to improved stock trays used in taking an impression for fabricating an apparatus to be installed in a mouth of a subject when a maker of foods, drugs or spices develops a product such as vitamin compound, nutrient, drug, spice and sweetener. This apparatus comprises a chamber with a semipermeable fine mesh membrane made of plastic or metal. The chamber may be attached to the inner side of an artificial tooth or a plate of a denture, or to a hidden area in a mouthpiece. The chamber may be provided at an edge position of a plate in a denture or mouthpiece. When the denture or mouthpiece is inserted in a mouth, the edge position faces a maxillary tuberosity in the case of maxilla (thus a parotid gland for providing saliva is open near the position), or faces a sublingual caruncle in the case of mandible (thus a sublingual gland for providing saliva is open near the position). Previously, a predetermined amount of molten material such as vitamin compound, nutrient, drug, spice and sweetener is stored in the chamber. Osmotic pressure disperses the material into saliva with passing time. The effects in keeping and improving the subject's health may be investigated on the base of the pre-calculated amount to be ingested in a day.

In prior art dentistry, taking an impression is carried out twice in a process of manufacturing a denture: a preliminary impression of a mouth is taken with a "stock tray" to manufacture an "individual tray" first, and then a precise impression is taken with the individual tray to make a model of the mouth. The denture is manufactured by use of the model.

Historically such stock trays for taking preliminary rough impressions of mouths were devised about the middle of the 19th century on the basis of dental knowledge in those days. The materials of the stock trays have been replaced with metal or plastic, but their shapes have been hardly improved up to now.

In many cases, the preliminary impression taken with a conventional stock tray becomes inaccurate at some key parts, which adversely affects substantially the precise impression taken with an individual tray. As a result, a denture not satisfactory to a dentist may be obtained thereby giving a patient a pain. Such situation may occur in the case of a complete denture or partial plate denture.

SUMMARY OF THE INVENTION

It is an object of the present invention to provide improved stock trays capable of accurately taking an impression of a mouth including key parts, thereby enabling dentists to take directly a precise impression without an individual tray.

In order to achieve the object, according to the present invention, an improved maxillary dental stock tray for taking an impression of a dentulous or edentulous mouth comprises: a small through hole at the front and central position in a side wall of the tray, said position in the tray inserted in a mouth being in the neighborhood facing an incisive papilla or a median frenum; a projecting plate at the convex and central position in a base of the tray, said position in the tray inserted in the mouth being in the neighborhood facing a median palatine raphe or a palatine foveola; projections at the rear edge positions in the base of the tray, said positions in the tray inserted in the mouth being in the neighborhood facing a hamular notch; and protuberances at the rear end positions in an outer surface of the side wall of the tray, said positions in the tray inserted in the mouth being in the neighborhood facing a maxillary tuberosity.

Preferably, said projecting plate is disk-shaped, said projections are sectorial and said protuberances are semi-conical.

The projecting plate, the projections and the protuberances, however, may have any shapes as long as they have respective functions as described below. The plate and the projections may be, for example, elliptic plate-shaped, rectangular plate-shaped with round corners or trapezoid plate-shaped. The protuberances may be, for example, semi-sphere or rectangular solid with round corners.

According to the present invention, an improved mandibular dental stock tray for taking an impression of a dentulous or edentulous mouth comprises: projecting plates at the rear end positions in an inner surface of an inner wall of the tray, said positions in the tray inserted in a mouth being in the neighborhood facing a mylohyoid muscle line; projections at the rear edge positions in a base of the tray, said positions in the tray inserted in the mouth being in the neighborhood facing a retromolar pad; a small through hole at the front and central position in the inner wall of the tray, said position in the tray inserted in the mouth being in the neighborhood facing a lingual frenum or a sublingual caruncle; and a small through hole at the front and central position in an outer wall of the tray, said position in the tray inserted in the mouth being in the neighborhood facing lower front teeth or a median part.

Preferably, said projecting plates are disk-shaped and said projections are sectorial.

The projecting plates, the projections and the protuberances, however, may have any shapes as long as they have respective functions as described below. The projecting plates and the projections may be, for example, elliptic plate-shaped, rectangular plate-shaped with round corners or trapezoid plate-shaped.

DETAILED DESCRIPTION OF THE PREFERRED EMBODIMENTS

Figure 1:
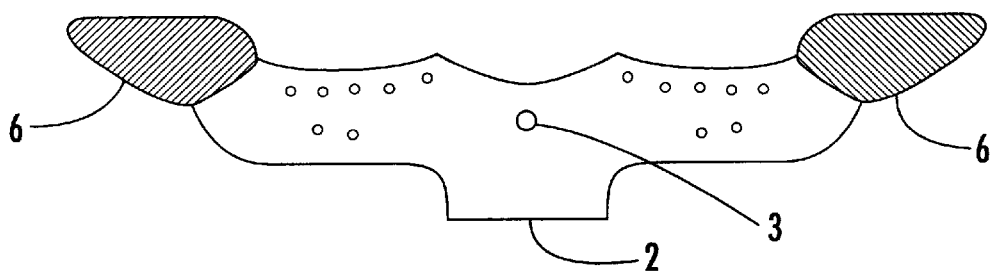
FIG. 1 is a front view of an improved maxillary stock tray for a dentulous mouth according to the present invention.

Before the explanation of the embodiments of the present invention with reference to the drawings, several considerations are given as follows:

i) The numeral values of "size", "length" and "angle" of respective parts in the embodiments are based on a standard adult. The present invention, however, may be applied to any person such as child, not standard adult, by scaling the shapes.

ii) The material of improved stock trays according to the present invention may be any ones that cause no allergy reaction in a mouth and have sufficient solidity.

iii) For an improved stock tray according to the present invention, a plurality of kinds of size may be offered. For example, the present invention may provide three kinds of trays, i.e. M (middle)-type, L (large)-type, and S (small)-type, or may provide any number of kinds of trays, for instance, XL, L, M, and S.

iv) In the drawings, hatching indicates improvements newly added to conventional stock trays. Thus the hatching does not indicate sections.

Moreover, it should be noted that it would be probably difficult for dentists to take impressions for (1) patients who tend to have strong deglutition reflexes or be allergic to the apparatus or material for impression taking, (2) patients who subconsciously dislike impression taking, (3) patients who are too old, and (4) patients who are too tired or just after recovery of diseases.

Now, the embodiments of the present invention are described below with reference to the drawings.

For reference, FIGS. 21–36 illustrate conventional stock trays: FIGS. 21–14, FIGS. 25–28, FIGS. 29–32 and FIGS. 33–36 are in the cases of a dentulous maxilla, a dentulous mandible, an edentulous maxilla and an edentulous mandible, respectively.

The conventional maxillary stock trays for a dentulous or edentulous mouth as shown in FIGS. 21–24 and 29–32 comprise a handle 44,64 and a body that is composed of a base 42,62 and a side wall 41,61. The handle 44,64 is attached to the front edge of the body. The central area 43,63 of the base 42,62 is convex and the side wall 41,61 surrounds the outer edge of the base except its rear edge.

The conventional mandibular stock trays for a dentulous or edentulous mouth as shown in FIGS. 25–28 and 33–36 comprise a handle 54,74 and a body that is composed of a base 53,73, an outer wall 51,71 and an inner wall 52,72. The handle 54,74 is attached to the front edge of the body. The base 53,73 is approximately U-shaped, the outer wall 51,71 surrounds the outer edge of the base 53,73 and the inner wall 52,72 surrounds the inner edge of the base 53,73.

Figure 2:
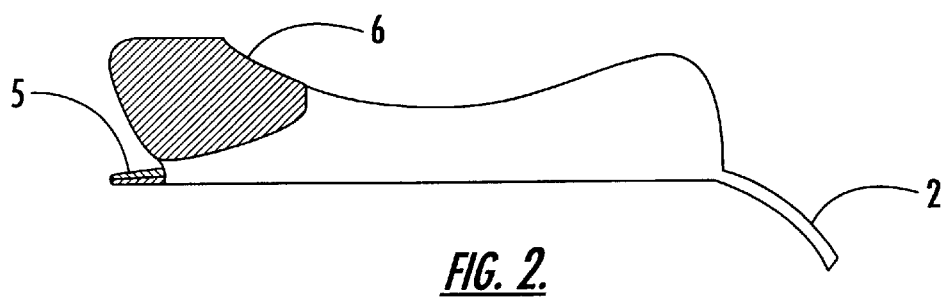
FIG. 2 is a left side view of the improved stock tray shown in FIG. 1.
Figure 3:
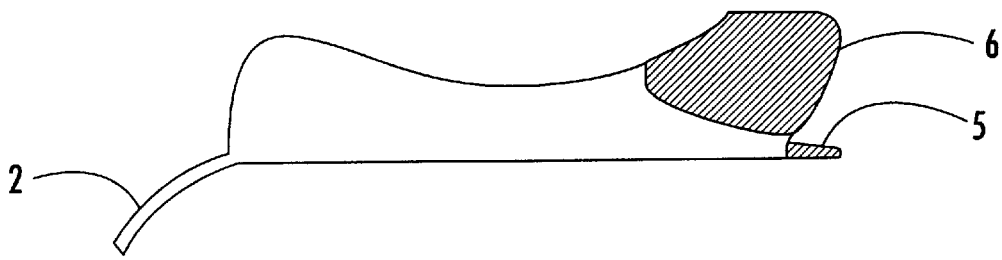
FIG. 3 is a right side view of the improved stock tray shown in FIG. 1.
Figure 4:
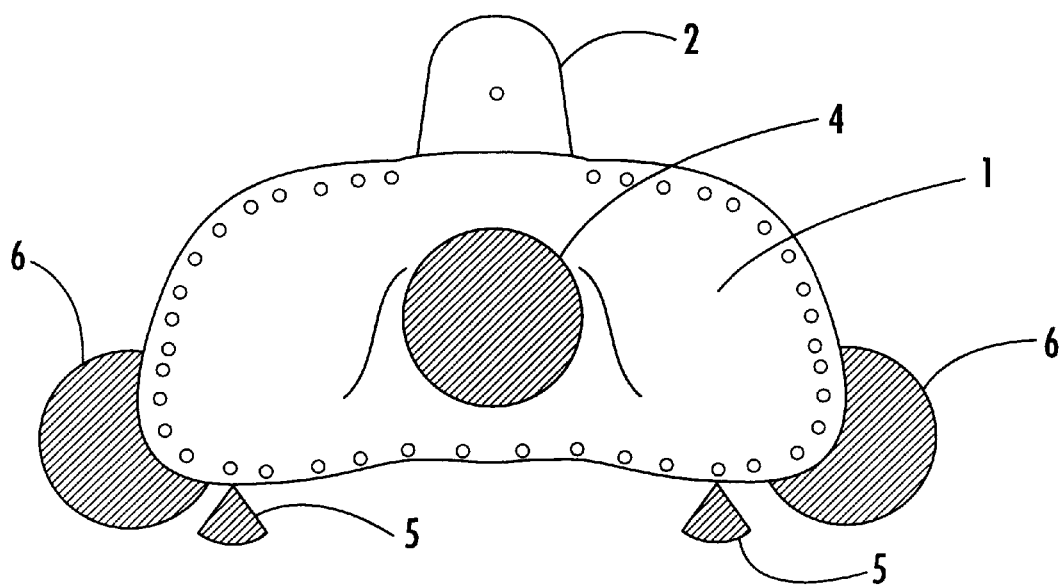
FIG. 4 is a plan view of the improved stock tray shown in FIG. 1.
Figure 5:
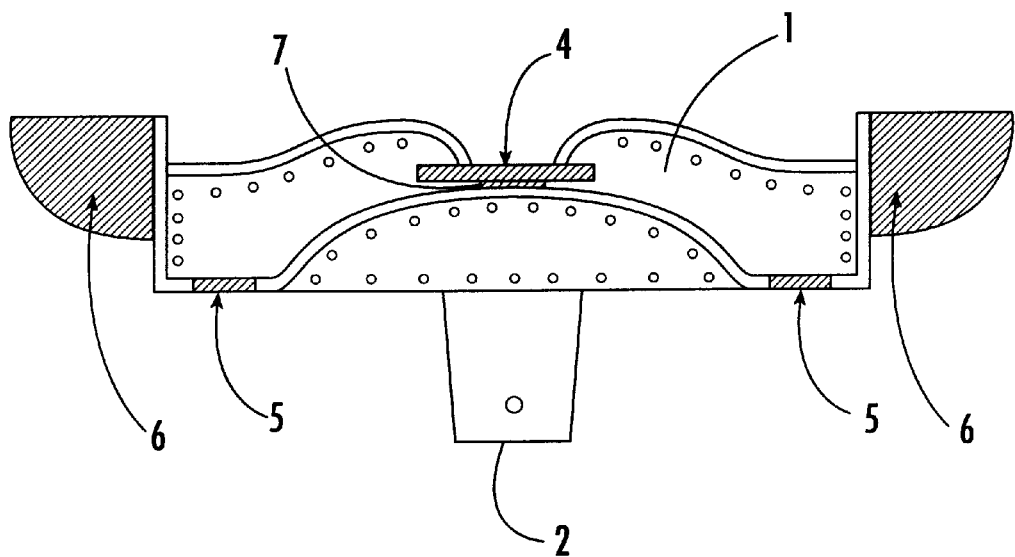
FIG. 5 is a rear view of the improved stock tray shown in FIG. 1.

FIGS. 1–5 illustrate an improved maxillary stock tray for a dentulous mouth according to the present invention; FIG. 1 is a front view, FIG. 2 is a left side view, FIG. 3 is a right side view, FIG. 4 is a plan view and FIG. 5 is a rear view thereof.

In FIGS. 1–5, reference numeral 3 indicates a small through hole provided at the front and central position in a side wall of the tray, said position being in the neighborhood facing an incisive papilla or a median frenum when the tray is inserted in a mouth. The through hole 3 improves the impression of the incisive papilla and the median frenum, and has a diameter of approximately 3 mm.

When the tray loaded with impression material is inserted in a mouth, a certain amount of impression material flows from the through hole 3 toward the lip side in the median part. Under this condition, an upper lip is kept slightly pressed until the impression material is hardened. After completion of hardening of the impression material, the tray is removed. With the help of the impression material flowed from the through hole 3, the position, shape and size of the incisive papilla and the median frenum are more clearly obtained in its impression. In the case where front teeth remain, the position, shape, size of the front teeth and the direction of tooth axis are more clearly obtained in its impression. Moreover, the impression material flowed and hardened from the through hole 3 prevent the separation of the impression material from the tray during removal of the tray from the mouth.

In FIGS. 1–5, reference numeral 4 indicates a projecting plate, or disk, provided at the convex and central position in a base of the tray, said position being in the neighborhood facing a median palatine raphe or a palatine foveola when said tray is inserted in the mouth. The disk 4 improves the impression of the median palatine raphe and the palatine foveola. The disk 4 is supported by a leg 7 having a diameter of about 2 mm. The leg 7 is located near the most projecting center position in the convex base, and directed to the median palatine raphe when the tray is inserted in the mouth.

The disk 4 prevent dentists from strongly pressing the tray against a palate, thereby facilitating the protection of the palate. If the tray is strongly pressed onto it, a mucous membrane of the palate will be injured by the tray, or the impression material will overflow causing unclear areas to the impression. Such drawback is eliminated by the disk 4.

The disk 4 improves prior art of impression taking in the following points:

(i) The first half of a median palatine raphe can be clearly impressed. This region is a hard palate. Thus, in the case where a plurality of teeth are missing, a relief chamber is usually provided to relieve an acute pain.

(ii) The second half of the median palatine raphe can be clearly impressed. This region is a soft palate, which significantly affects the patient's pronunciation and the stability of a denture.

(iii) A palatine foveola, which is a reference region for determining the rear edge of a denture, can be clearly impressed.

In FIGS. 1–5, reference numeral 5 indicates sectorial projections provided at the rear edge positions in the base of the tray, said positions being in the neighborhood facing a hamular notch when said tray is inserted in the mouth. The projections 5 improve the impression of the hamular notches.

The projections 5, which is added to a conventional tray at the areas facing the rear edges of maxillary tuberosities, allow the clear impression of the hamular notches in size, shape and position. The sector shape of the projections 5 is adaptable to the hamular notches which are floating and movable mucous membranes. If a plate edge of a denture rides on the hamular notches, the denture will become unstable; hence, dentures should be designed so as to avoid such situation.

Figure 37A:
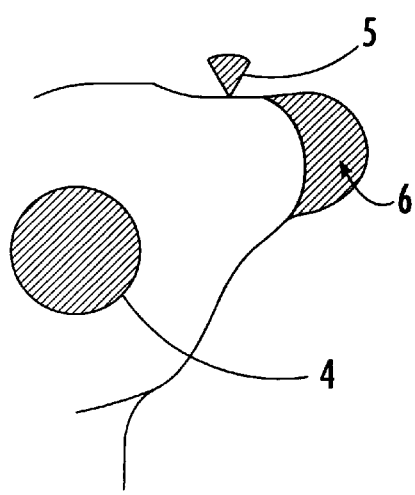
FIG. 37 illustrates a sectorial projection of the improved maxillary stock tray for a dentulous mouth according to the present invention.
Figure 37B:
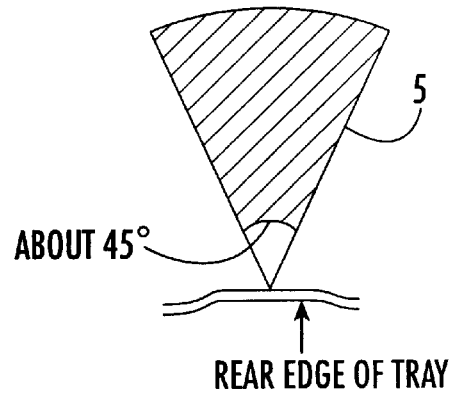

FIGS. 37a and 37b are a partially enlarged plan view of the improved maxillary stock tray for a dentulous mouth and an enlarged view of the sectorial projection 5, respectively. The projection 5 is provided at the rear edge of the base of the tray, as shown in FIG. 37a, and has an angle of about 45 degrees between its two sides, as shown in FIG. 37b.

In FIGS. 1–5, reference numeral 6 indicates semi-conical protuberances provided at the rear end positions in an outer surface of the side wall of the tray, said positions being in the neighborhood facing a maxillary tuberosity when said tray is inserted in the mouth. The protuberances 6 improve the impression of the maxillary tuberosities.

Figure 38:
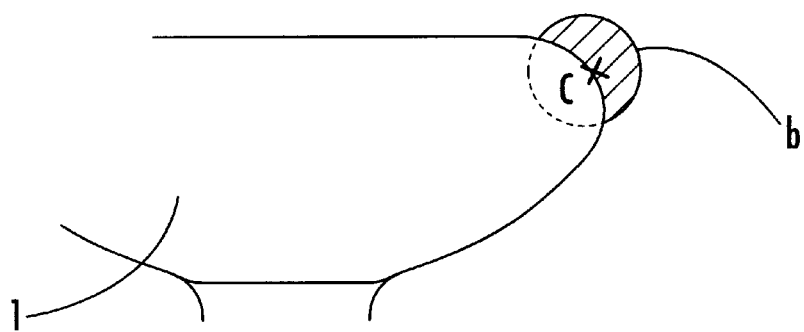
FIG. 38 illustrates a semi-conical protuberance of the improved stock tray according to the present invention.

FIG. 38 is a partial plan view of the improved tray showing an example of the protuberance 6. In this figure, point C indicates a maximum protrusion area in a conventional tray, facing the maxillary tuberosity when the tray is inserted in the mouth. The protuberances 6 in the shape as shown in FIG. 38 newly added to the conventional tray allow mucous membranes near maxillary tuberosities to be pushed away in cheeks. The impression material enters the space where the mucous membranes are pushed away during impression taking, as a result, a clear impression of the maxillary tuberosities can be taken surely.

In FIG. 38, a plan view, the protuberance 6 may be regarded as an approximately half circle indicated by hatching with a center point C. In the case of adults, the diameter of the half circle is about 24 mm. The center point C is a maximum protrusion point in the conventional tray, facing the maxillary tuberosity when the tray is inserted in the mouth.

Figure 39A:
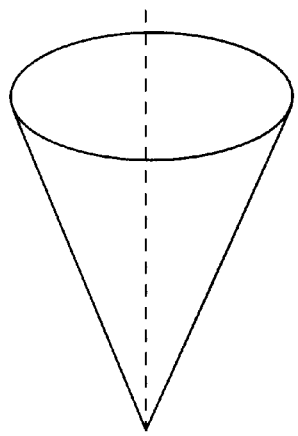
FIG. 39 illustrates the semi-conical protuberance of the improved stock tray according to the present invention.
Figure 39B:
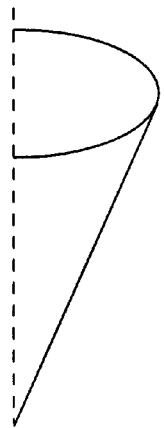
Figure 39C:
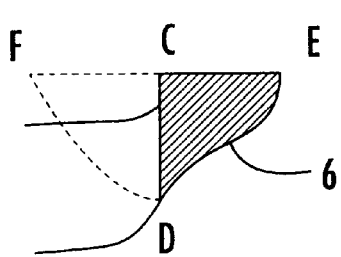
Figure 39D:
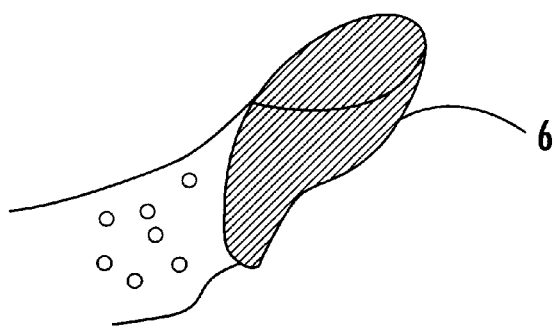

FIGS. 39a–39d show that the protuberance 6 is in the shape of an approximately half cone. For reference, FIG. 39a illustrates a general cone, and FIG. 39b illustrates half of the cone, or a semi-cone. FIGS. 39c and 39d illustrate the protuberance 6 by hatching in a partial front view and a partial perspective view, respectively. It can be seen from FIGS. 39a–39d that the protuberance 6 newly added to the conventional tray is approximately semi-conical.

Figure 6:
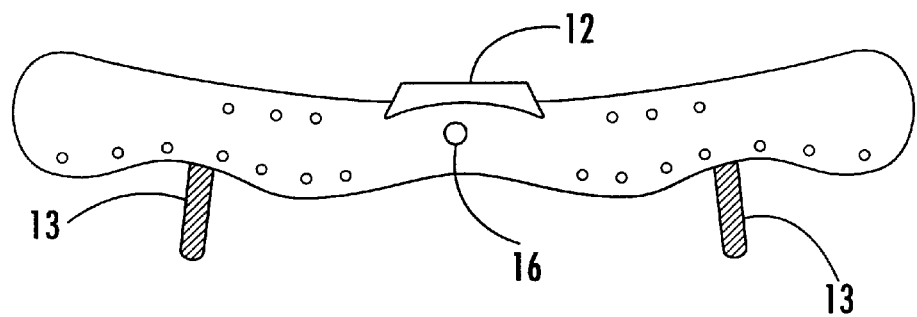
FIG. 6 is a front view of an improved mandibular stock tray for a dentulous mouth according to the present invention.
Figure 7:
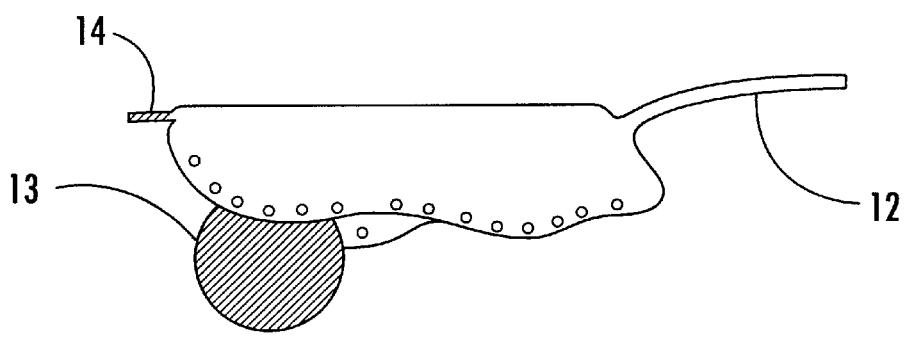
FIG. 7 is a left side view of the improved stock tray shown in FIG. 6.
Figure 8:
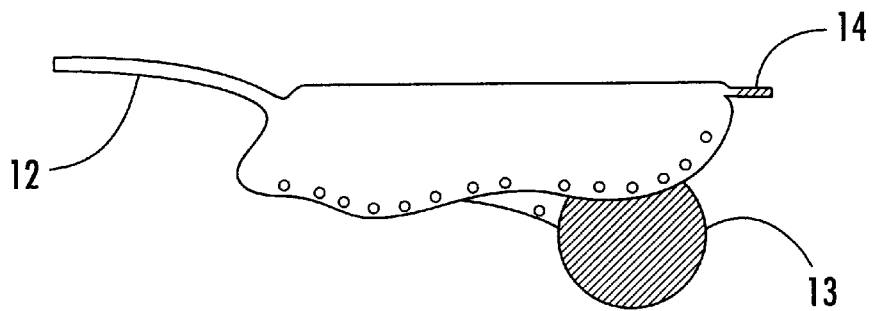
FIG. 8 is a right side view of the improved stock tray shown in FIG. 6.
Figure 9:
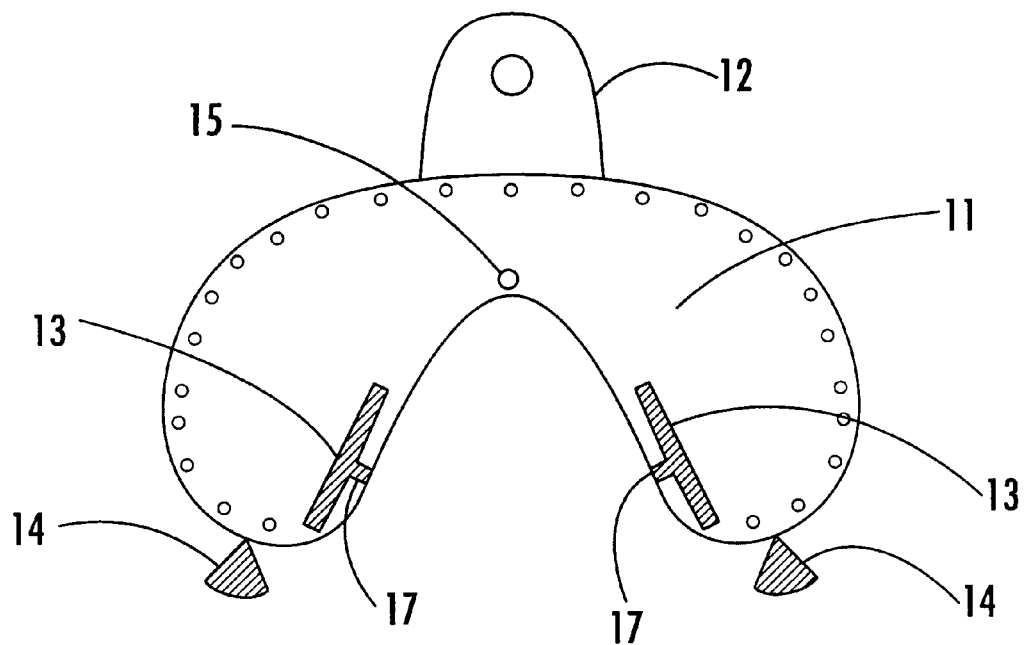
FIG. 9 is a base view of the improved stock tray shown in FIG. 6.
Figure 10:
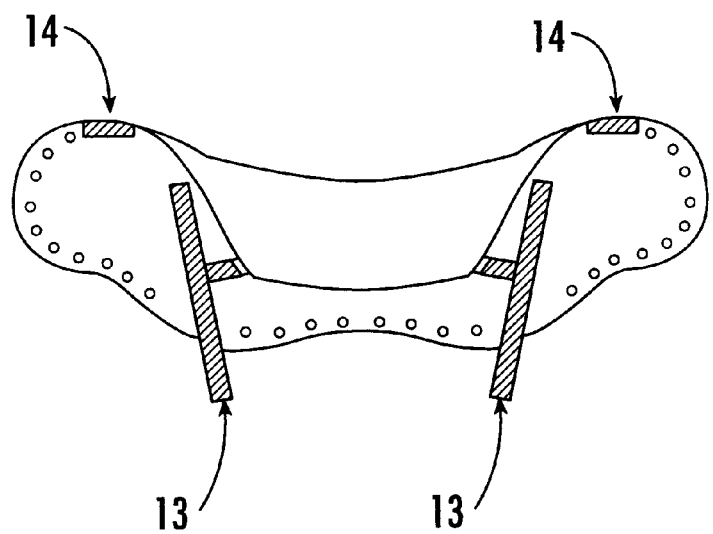
FIG. 10 is a r ear view of the improved stock tray shown in FIG. 6.

FIGS. 6–10 illustrate an improved mandibular stock tray for a dentulous mouth according to the present invention; FIG. 6 is a front view, FIG. 7 is a left side view, FIG. 8 is a right side view, FIG. 9 is a plan view and FIG. 10 is a rear view thereof.

In FIGS. 6–10, reference numeral 13 indicates projecting plates, or disks, provided at the rear end positions in an inner surface of an inner wall of the tray, said positions being in the neighborhood facing a mylohyoid muscle line when said tray is inserted in a mouth. The disks 13 improve the impression of the mylohyoid muscle lines.

The disks 13 are newly added by legs 17 to a conventional stock tray made on the basis of the shape of a mandible. The legs 17 are provided at the rear end positions in the inner surface of the inner wall of the improved tray, said positions being in correspondence with a mandibular angle when the tray is inserted in the mouth. One end of the leg 17 is attached to the center of the disk 13. The attached disks 13 allow a clear impression of the mylohyoid lines.

Figure 40A:
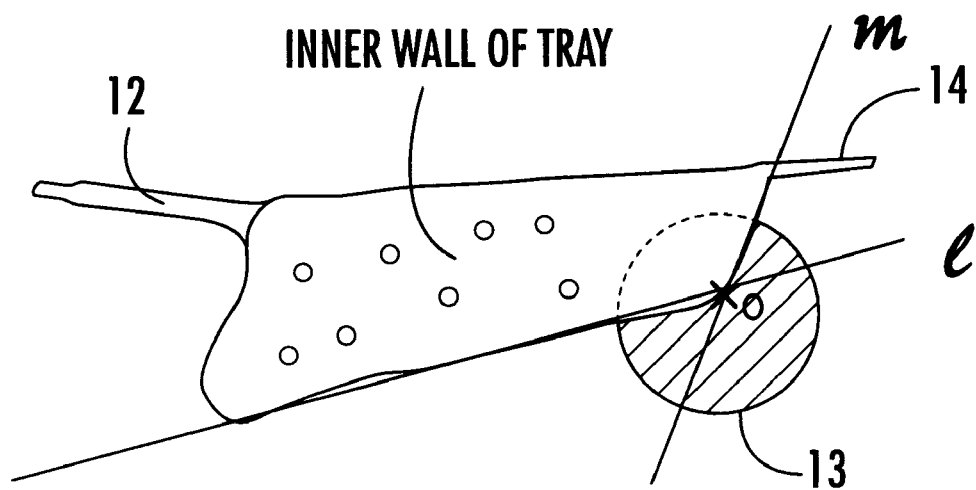
FIG. 40 illustrates the shape and position o of a disk-shaped plate of the improved stock tray according to the present invention.
Figure 40B:
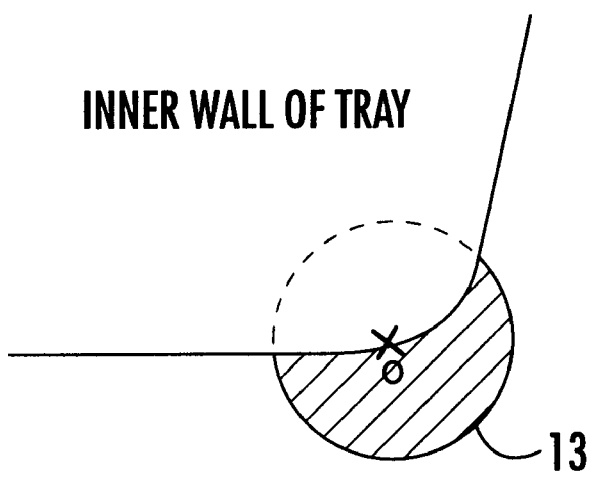

FIG. 40a illustrates an outer surface of the inner wall of the tray, for explanation of the shape and position of the disk 13, and FIG. 40b is an enlarged view thereof. The center of the disk 13 is point O or cross point of virtual tangents L and M, which point nearly corresponds to the most curved point in a conventional tray, as shown in these figures. In the case of adults, the disk 13 has a diameter of about 24 mm.

The reason why the leg 17 is located on the point O in FIG. 40a is that tongue pressure is minimum at this point in view of many clinical experiences of taking an impression of a mandible. Thus, the disk 13 forming a "wall" against the tongue pressure at this point allows stably taking an impression of the mylohyoid line and the region facing the rear edge of a denture.

When the improved tray having the disks 13 is inserted in the mouth, the impression material enters and hardens between an alveolar ridge and the tongue, so that the impression of the mylohyoid lines and its periphery can be taken clearly and surely.

Figure 41A:
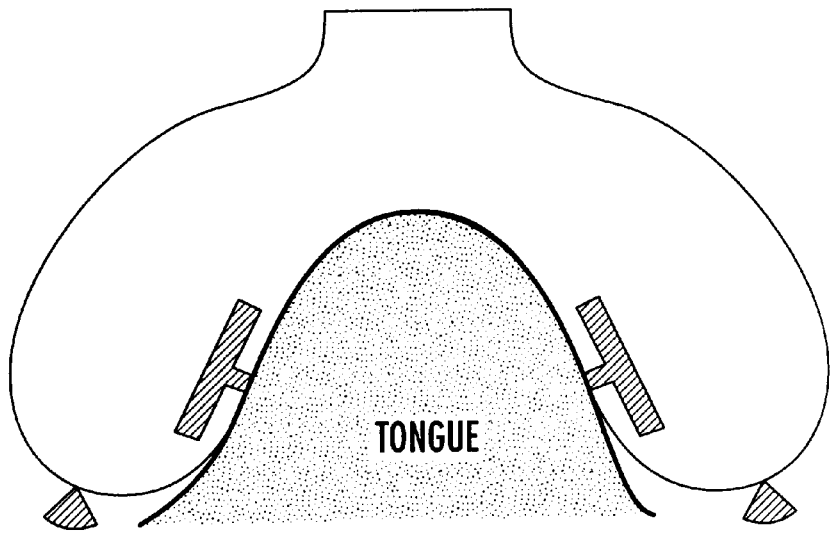
FIG. 41 illustrates the disk-shaped plates positioned inside and outside an alveolar ridge for comparison.
Figure 41B:
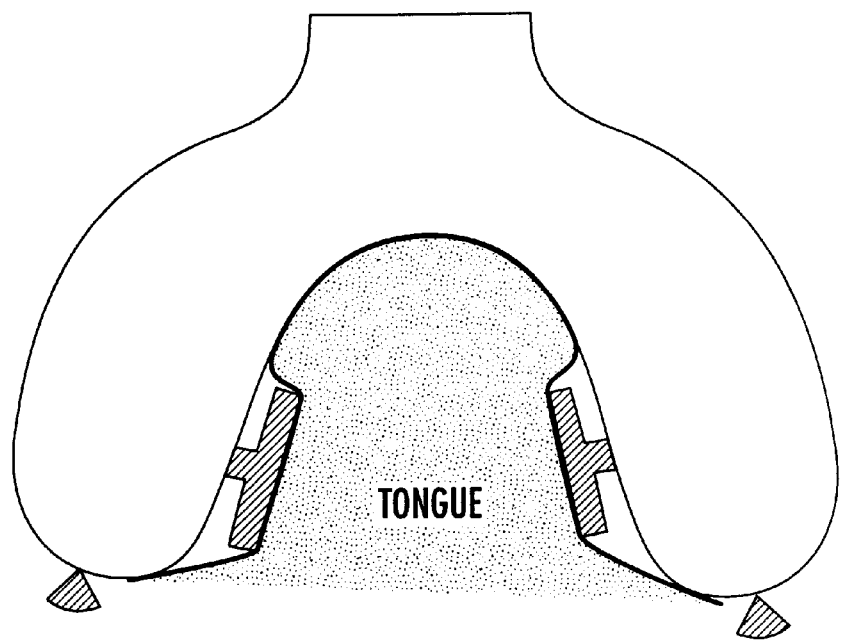

It is remarkable that the disks 13 are located at the inner surface of the inner wall of the tray, corresponding to the alveolar ridge, as shown in FIG. 41a. Even if high pressure is given by the tongue, the disks 13 function as a "wall" to prevent the influence of the pressure. If the disks 13 are located except at the inner surface facing the alveolar ridge, i.e. at an outer surface of the inner wall, as shown in FIG. 41b, a patient cannot settle the tongue at a stable position feeling the disk burdensome, and will increase the tongue pressure to push away the tray.

Similarly to the disk 4 of the improved maxillary stock tray for a dentulous mouth, the disks 13 provided at the inner surface of the inner wall makes it easy for dentists to protect the alveolar ridge without strongly pressing the tray against it during impression taking. If the tray is pressed strongly, a mucous membrane of the alveolar ridge will be injured by the tray, or the impression material will overflow to cause unclear areas to the resultant impression. Such drawback can be eliminated by the disks 13. Anyhow, it is important for dentists to retain the tray softly with pressure as low as possible.

When the improved tray not loaded with impression material is inserted in a mouth for checking the adaptability of the tray itself, the following two kinds of patients may be considered:

(i) patients who do not tense their tongues; and (ii) patients who dislike impression taking. Such patients would push out or press the trays with tongues tensed because of pain.

In the case of (i), satisfactory impressions can be obtained.

In the case of (ii), if dentists give the patients the following instructions to relax them, good impressions can be obtained:

(I) raising the tongue toward the palate;

(II) holding the tongue between upper and lower lips; and (III) putting the tongue out of the mouth.

In FIGS. 6–10, reference numeral 14 indicates sectorial projections provided at the rear edge positions in the base of the tray, said positions being in the neighborhood facing a retromolar pad when said tray is inserted in the mouth. The projections 14 improve the impression of the retromolar pads.

The retromolar pad, namely, the region corresponding to the rear edge of the alveolar ridge of the mandible is floating and movable well, similarly to the hamular notch. As a result, when a denture is mounted, air enters the space between the retromolar pad and the denture, thereby adversely affecting the stability. Since the inside of the mucous membrane in this region is composed of tendons, a pain is not caused by the denture. If the plate edge of the denture is placed away from the retromolar pad, a pain will be caused immediately. Only at this region among the alveolar ridge of the mandible, no pain is caused by the denture. When a pain is caused at other regions in the alveolar ridge, it is possible to transmit the pain to the pad region. Most dentists currently adjust dentures taking the pad position into consideration.

The reason why the sectorial shape is adopted for the projections 14 is that the projection buried into the impression material form a core to prevent the hardened material to be distorted.

Figure 42A:
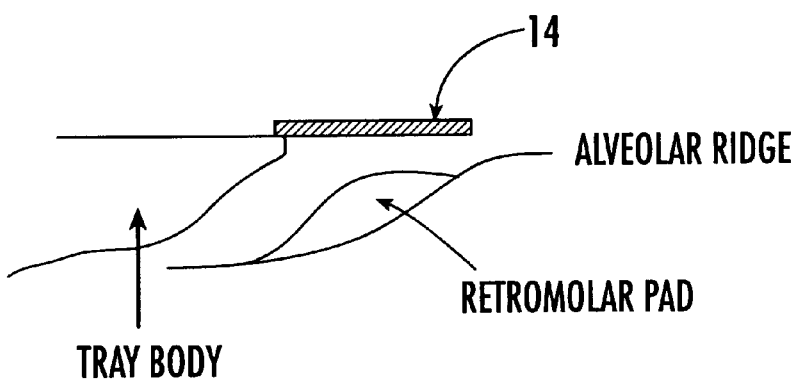
FIG. 42 illustrates the sectorial projection of the improved stock tray according to the present invention.
Figure 42B:
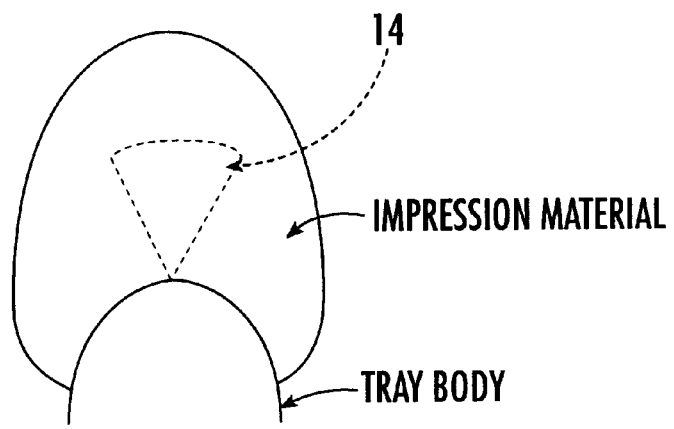

FIG. 42a and FIG. 42b illustrate the sectorial projection 14 in a partial side view and a partial plan view.

In FIGS. 6–10, reference numeral 15 indicates a small through hole provided at the front and central position in the inner wall of the tray, said position being in the neighborhood facing a lingual frenum or a sublingual caruncle when said tray is inserted in the mouth. The through hole 15 improves the impression of the lingual frenum.

The through hole 15 allows the impression material to flow out and harden, thereby contributing to a clear impression. The denture should be designed so as to avoid the placement on the lingual frenum. If the plate edge of the denture is placed on the lingual frenum, a pain will be caused and the denture cannot be retained stably.

In FIGS. 6–10, reference numeral 16 indicates a small through hole provided at the front and central position in the outer wall of the tray, said position being in the neighborhood facing lower front teeth or a median region when said tray is inserted in the mouth. The through hole 16 improves the impression of the median region of the dentulous mandible.

When the tray loaded with the impression material is inserted in the mouth, the material flows out of the hole 16 toward the lip side of the median region of the mandible. If the front teeth remain in the mandible, after the flowing the lip side should be kept slightly pressed with a lower lip until hardening. The tray is removed after hardening. The impression material flowed out of the hole 16 ensures a clear impression of the front teeth and the median region of the mandible.

Figure 11:
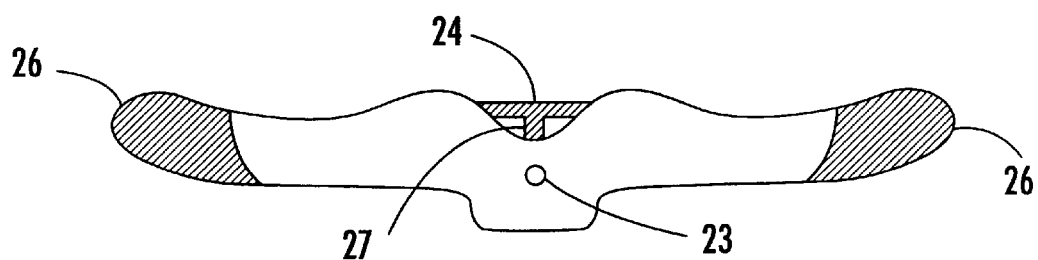
FIG. 11 is a front view of an improved maxillary stock tray for an edentulous mouth according to the present invention.
Figure 12:
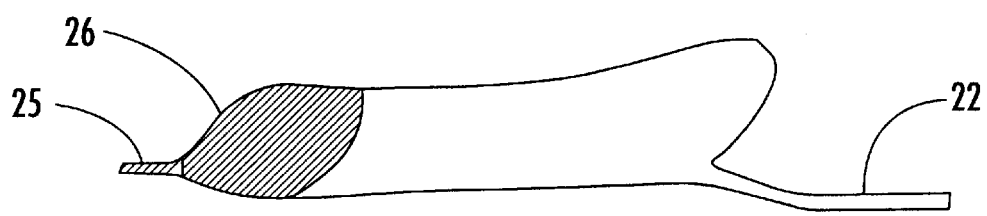
FIG. 12 is a left side view of the improved stock tray shown in FIG. 11.
Figure 13:
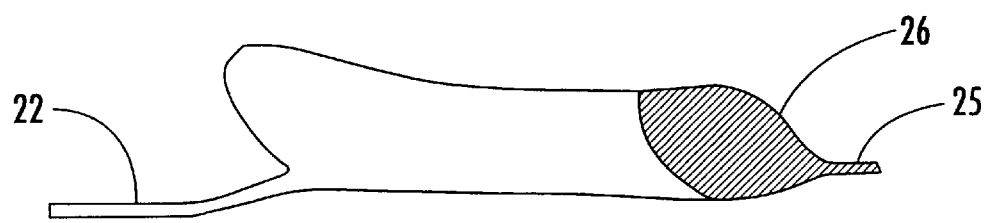
FIG. 13 is a right side view of the improved stock tray shown in FIG. 11.
Figure 14:
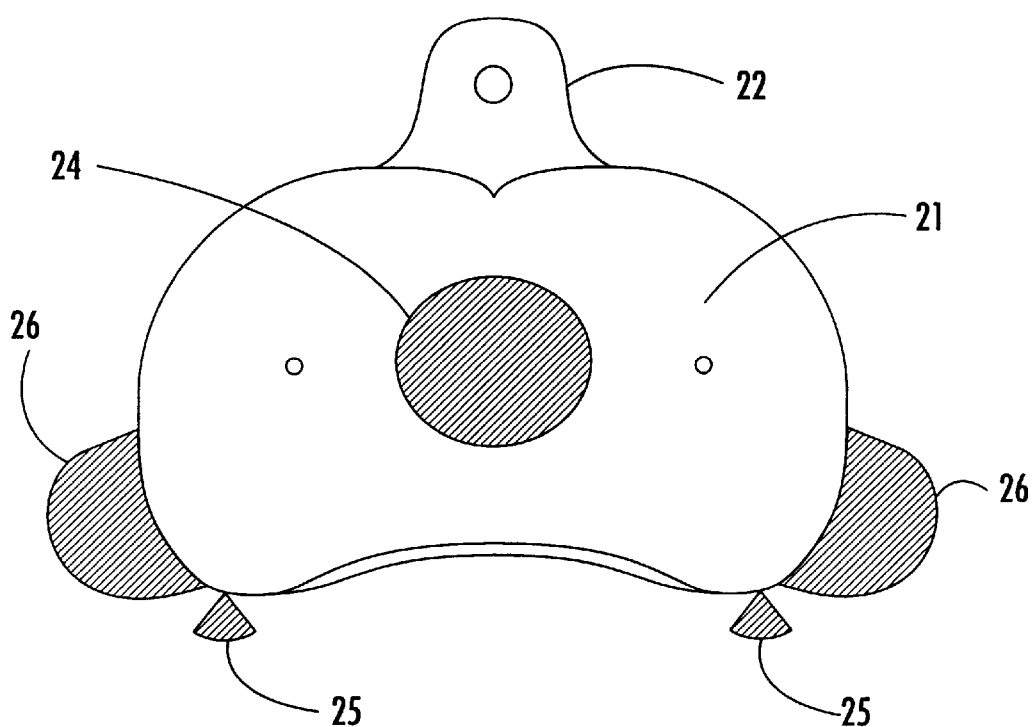
FIG. 14 is a plan view of the improved stock tray shown in FIG. 11.
Figure 15:
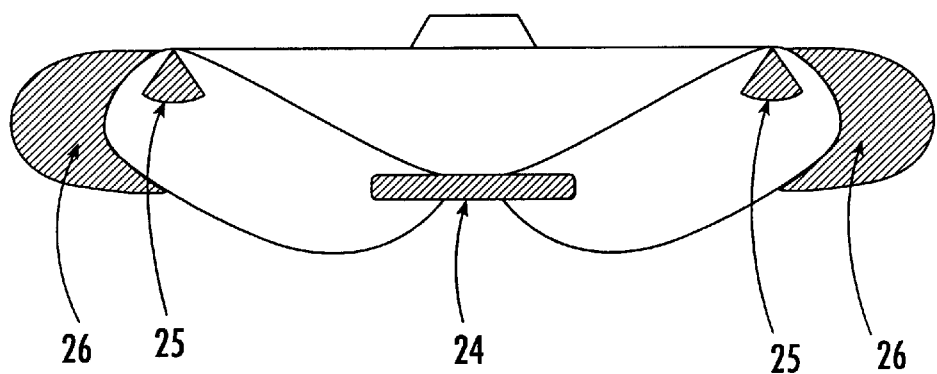
FIG. 15 is a rear view of the improved stock tray shown in FIG. 11 being upside down.

FIGS. 11–15 illustrate an improved maxillary stock tray for an edentulous mouth according to the present invention; FIG. 11 is a front view, FIG. 12 is a left side view, FIG. 13 is a right side view, FIG. 14 is a plan view and FIG. 15 is a rear upside-down view thereof.

In FIGS. 11–15, reference numeral 23 indicates a small through hole provided at the front and central position in a side wall of the tray, said position being in the neighborhood facing an incisive papilla or a median frenum when said tray is inserted in a mouth. The through hole 23 improves the impression of the incisive papilla and the median frenum.

The impression of the incisive papilla is important for dentists to determine the position of the front teeth in the case of manufacture of a complete denture. The protrusion of the incisive papilla contributes to the stability of the denture. The denture should be designed so as to avoid the placement on the median frenum, because if the plate edge of the denture is placed on the frenum, an acute pain will be caused, thereby making the denture unstable.

When the tray loaded with the impression material is inserted in the mouth for taking an impression, a certain amount of material flows out from the through hole 23. The material flowed from the through hole 23 ensures a clear impression of the incisive papilla and the median frenum.

In FIGS. 11–15, reference numeral 24 indicates a projecting plate, or disk, provided at the convex and central position in the base of the tray, said position being in the neighborhood facing a median palatine raphe or a palatine foveola when said tray is inserted in the edentulous mouth. The disk 24 improves the impression of the median palatine raphe and the palatine foveola.

The disk 24 has the same shape, position and function as those of the disk 4 in the improved maxillary stock tray for a dentulous mouth. In the case of the edentulous mouth, the tray should be retained at lower pressure than that applied to the tray for the dentulous mouth during impression taking, because the edentulous mouth has not such alveolar ridge as contained in the dentulous mouth but a mere alveolar ridge.

In FIGS. 11–15, reference numeral 25 indicates sectorial projections provided at the rear edge positions in the base of the tray, said positions being in the neighborhood facing a hamular notch when said tray is inserted in the mouth. The projections 25 improve the impression of the hamular notches in the edentulous mouth.

The projections 25 have the same shape, position and function as those of the projections 5 in the improved maxillary stock tray for a dentulous mouth. In the case of the edentulous mouth, the dentists should retain the tray at no pressure in such a way that the projections are not touched strongly to a mucous membrane, because the alveolar ridge of the edentulous mouth is lower than that of the dentulous mouth.

In FIGS. 11–15, reference numeral 26 indicates semiconical protuberances provided at the rear end positions in an outer surface of the side wall of the tray, said positions being in the neighborhood facing a maxillary tuberosity when said tray is inserted in the mouth. The protuberances 26 improve the impression of the maxillary tuberosities in the edentulous mouth.

The protuberances 26 have the same shape, position and function as those of the protuberances 6 of the improved maxillary stock tray for a dentulous mouth.

In the case of patients who have maxillary tuberosities atrophied and almost lost, dentists intend to press the trays strongly or load the trays with a small or large amount of impression material, aiming at a clear impression. This would lead to an impression including unclear areas or an acute pain on the patients. The dentists should load the trays with an appropriate amount of impression material and softly retain the trays at no pressure.

Figure 16:
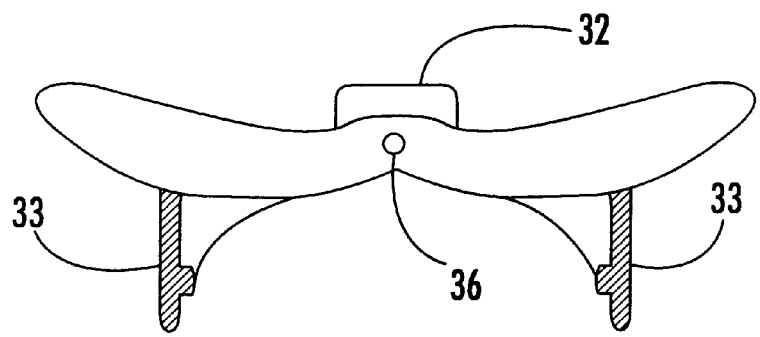
FIG. 16 is a front view of an improved mandibular stock tray for an edentulous mouth according to the present invention.
Figure 17:
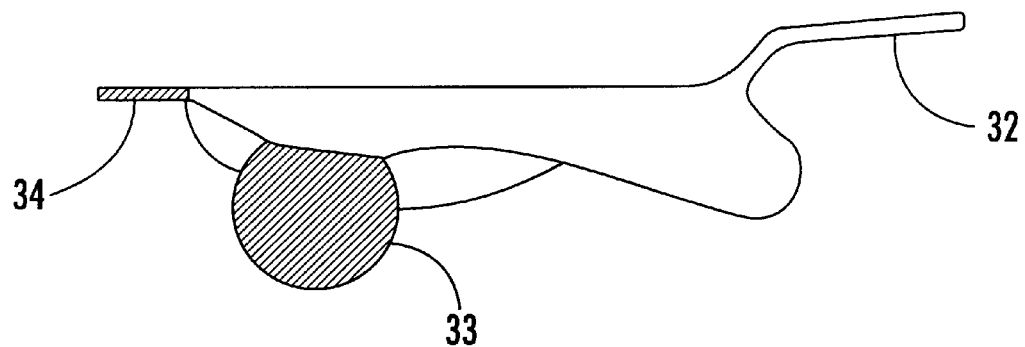
FIG. 17 is a left side view of the improved stock tray shown in FIG. 16.
Figure 18:
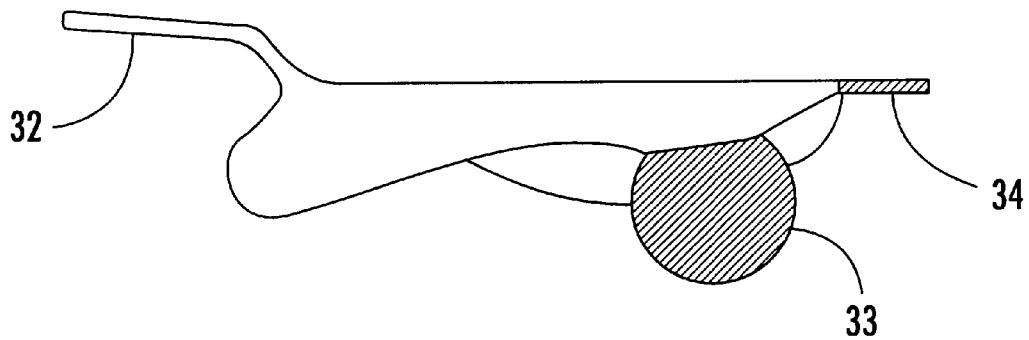
FIG. 18 is a right side view of the improved stock tray shown in FIG. 16.
Figure 19:
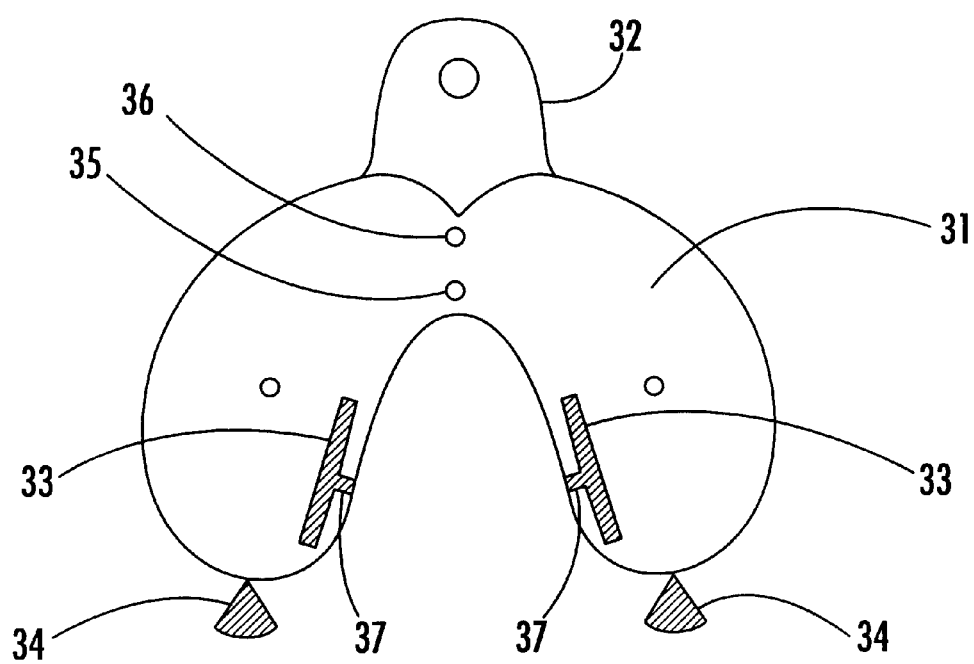
FIG. 19 is a base view of the improved stock tray shown in FIG. 16.
Figure 20:
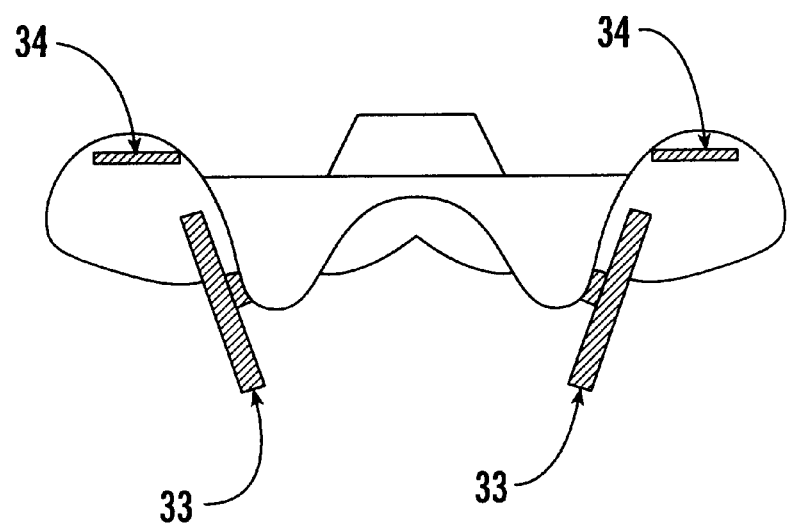
FIG. 20 is a rear view of the improved stock tray shown in FIG. 16.
Figure 21:
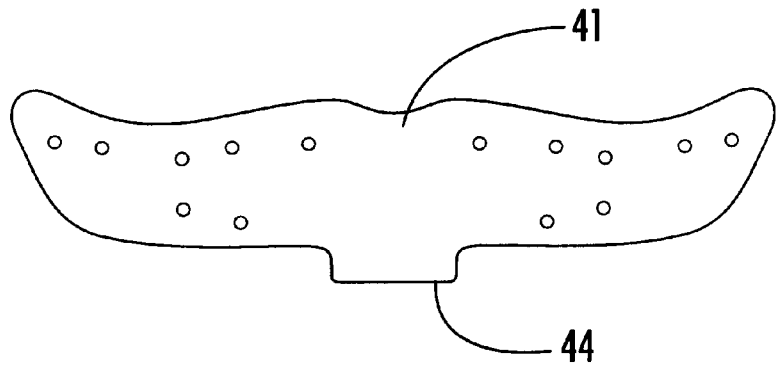
FIG. 21 is a front view of a maxillary stock tray for a dentulous mouth according to prior art.
Figure 22:
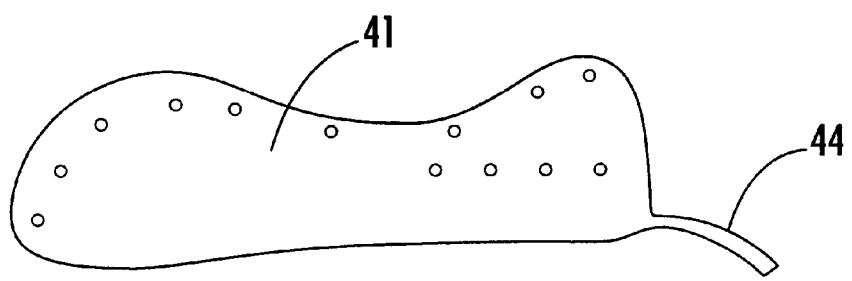
FIG. 22 is a left side view of the stock tray shown in FIG. 21.
Figure 23:
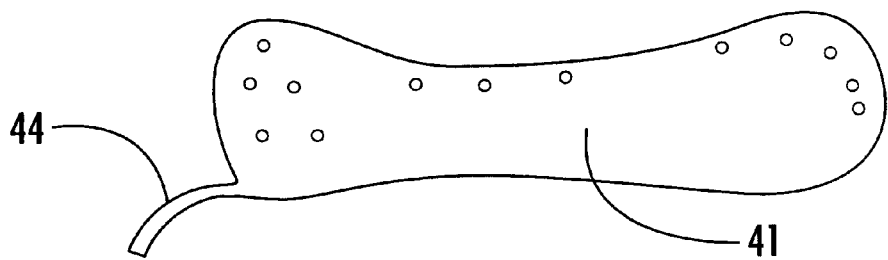
FIG. 23 is a right side view of the stock tray shown in FIG. 21.
Figure 24:
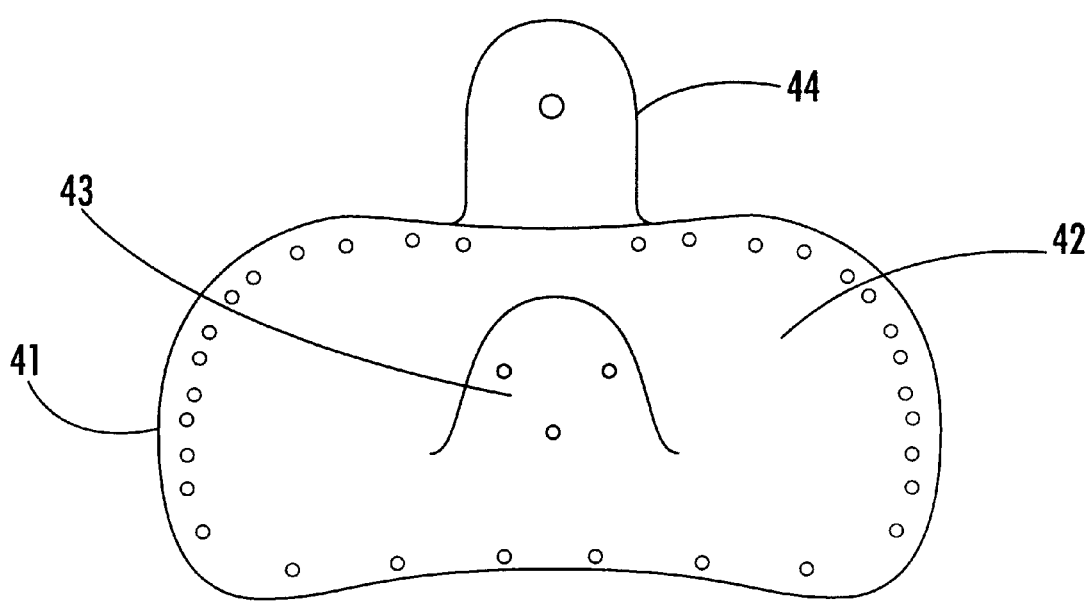
FIG. 24 is a plan view of the stock tray shown in FIG. 21.
Figure 25:
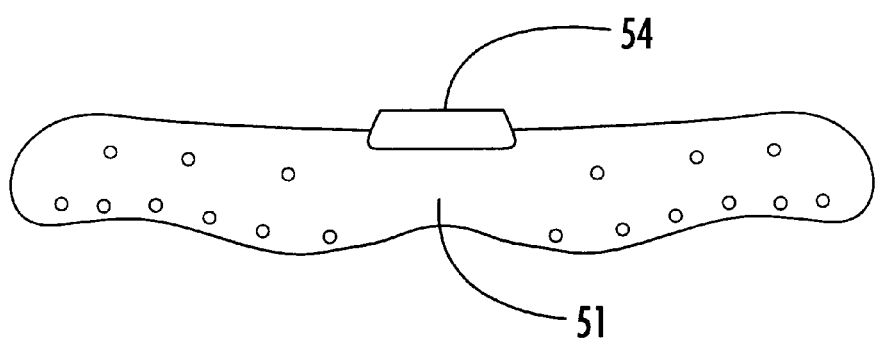
FIG. 25 is a front view of a mandibular stock tray for a dentulous mouth according to prior art.
Figure 26:
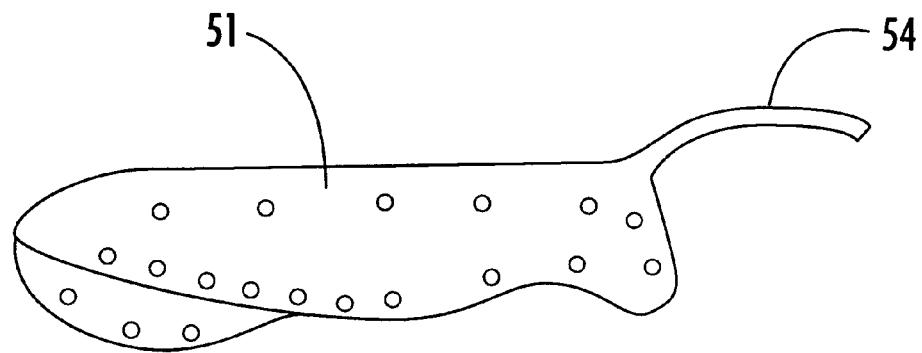
FIG. 26 is a left side view of the stock tray shown in FIG. 25.
Figure 27:
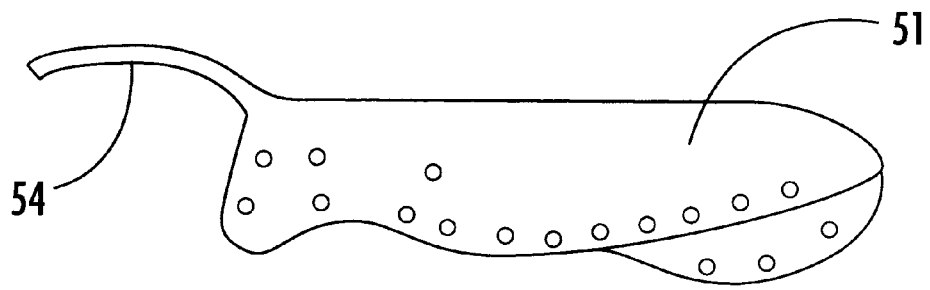
FIG. 27 is a right side view of the stock tray shown in FIG. 25.
Figure 28:
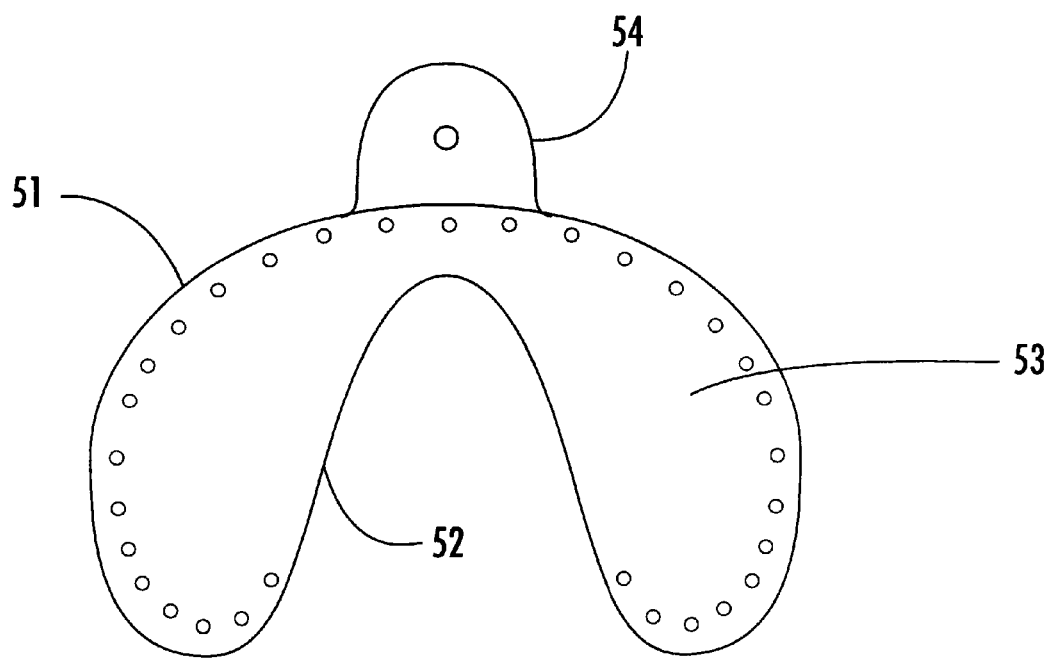
FIG. 28 is a base view of the stock tray shown in FIG. 25.
Figure 29:
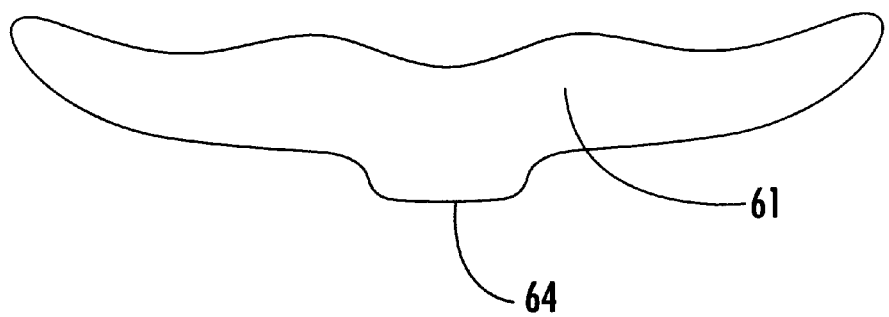
FIG. 29 is a front view of a maxillary stock tray for an edentulous mouth according to prior art.
Figure 30:
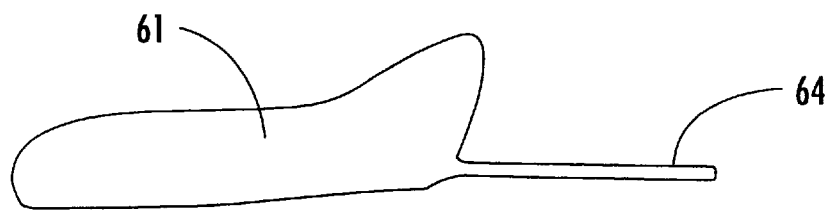
FIG. 30 is a left side view of the stock tray shown in FIG. 29.
Figure 31:
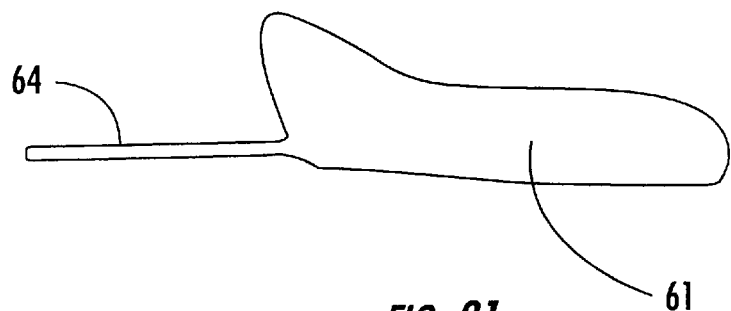
FIG. 31 is a right side view of the stock tray shown in FIG. 29.
Figure 32:
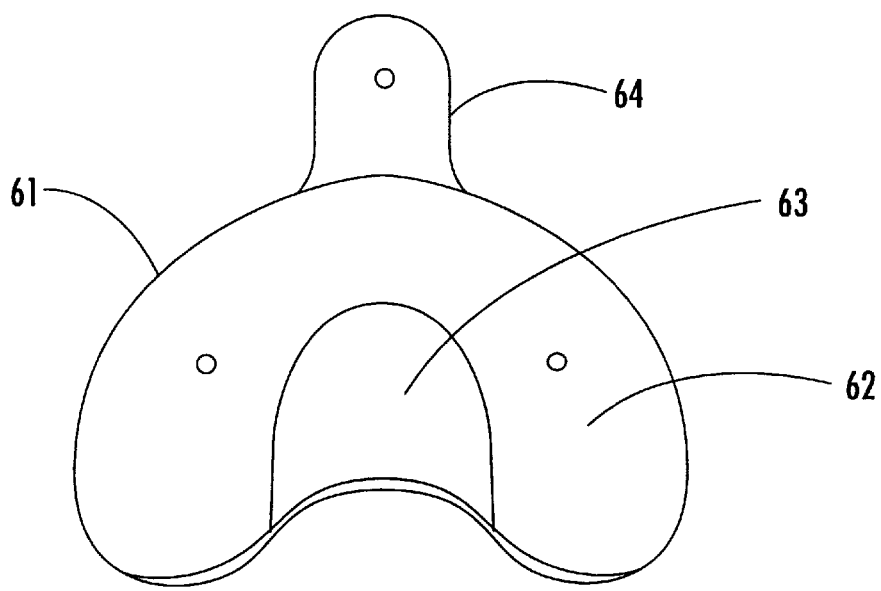
FIG. 32 is a plan view of the stock tray shown in FIG. 29.
Figure 33:
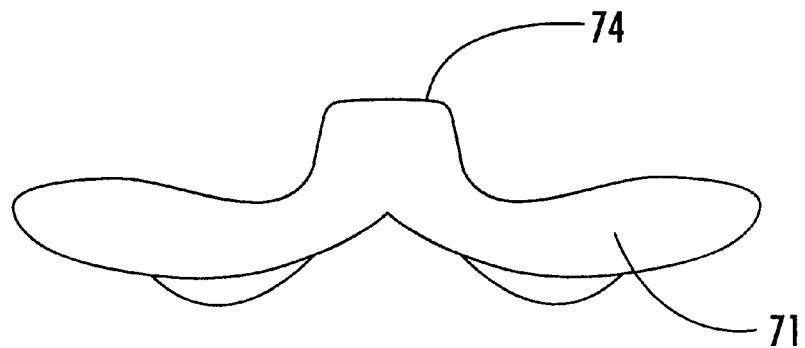
FIG. 33 is a front view of a mandibular stock tray for an edentulous mouth according to prior art.
Figure 34:
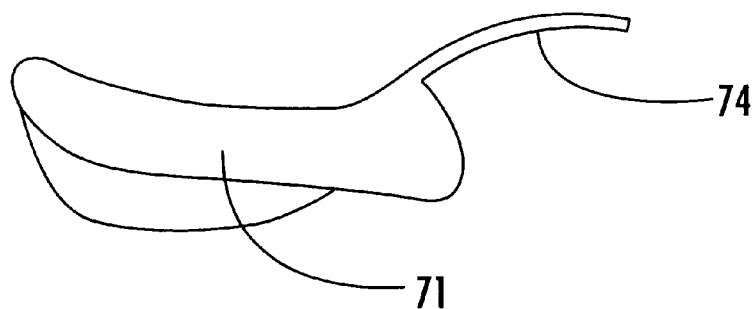
FIG. 34 is a left side view of the stock tray shown in FIG. 33.
Figure 35:
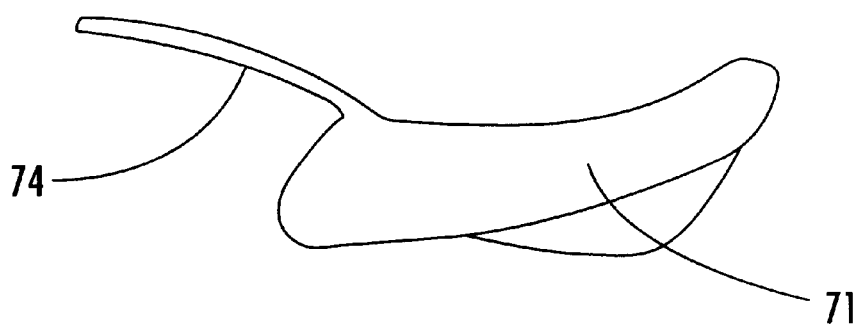
FIG. 35 is a right side view of the stock tray shown in FIG. 33.
Figure 36:
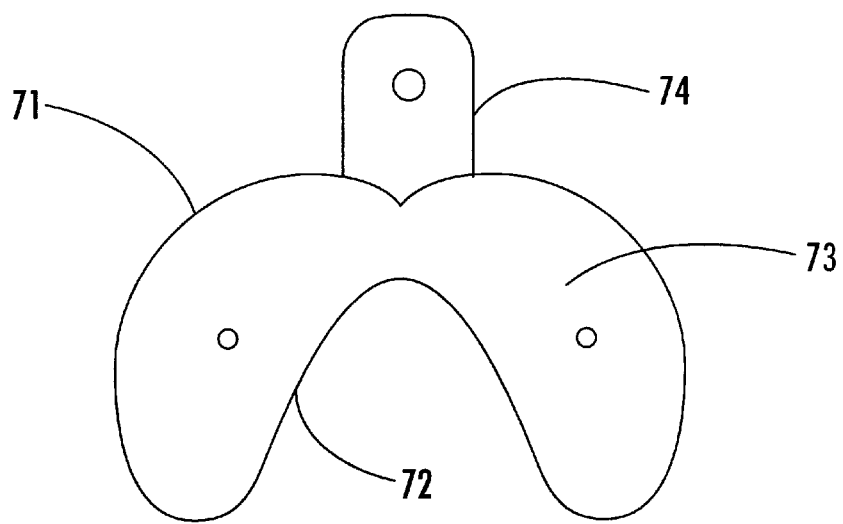
FIG. 36 is a base view of the stock tray shown in FIG. 33.

FIGS. 16–20 illustrate an improved mandibular stock tray for an edentulous mouth according to the present invention; FIG. 16 is a front view, FIG. 17 is a left side view, FIG. 18 is a right side view, FIG. 19 is a plan view and FIG. 20 is rear view thereof.

In FIGS. 16–20, reference numeral 33 indicates projecting plates, or disks, provided at the rear end positions in an inner surface of an inner wall of the tray, said positions being in the neighborhood facing a mylohyoid muscle line when said tray is inserted in a mouth. The disks 33 improve the impression of the mylohyoid muscle lines in the edentulous mouth.

The disks 33 have the same shape, position and function as those of the disks 13 in the improved mandibular stock tray for a dentulous mouth.

In the case of the edentulous mouth, patients often have alveolar ridges wholly atrophied or almost reduced. In these cases, dentists intend to load the trays with a very small or large amount of impression material or press the trays strongly, aiming at a clear impression of the alveolar ridges. If such actions are done with the improved tray, the resultant impression will not show a precise impression of the alveolar ridge, or the patients will be pained and dislike dental treatment. Thus the dentists should keep the trays softly at no pressure during impression taking.

In FIGS. 16–20, reference numeral 34 indicates sectorial projections provided at the rear edge positions in the base of the tray, said positions being in the neighborhood facing a retromolar pad when said tray is inserted in the mouth. The projections 34 improve the impression of the retromolar pads in the edentulous mouth.

The projections 34 have the same shape, position and function as those of the projections 14 in the improved mandibular stock tray for a dentulous mouth.

In the case of the edentulous mouth, the retromolar pads are important in stability of a complete denture. This is because if air enters the space between the retromolar pads and the denture, adhesion force against a mucous membrane of the alveolar ridge will be lost and the denture cannot be kept to the mucous membrane. Thus, a precise impression of the retromolar pads is required.

If the tray is pressed strongly or is loaded with a very small or large amount of impression material, the resultant impression will not show a precise impression of the alveolar ridge of the mandible, or the mucous membrane of the alveolar ridge will be injured by the tray. Thus, dentists should load the trays with an appropriate amount of impression material and keep them softly at no pressure.

In FIGS. 16–20, reference numeral 35 indicates a small through hole provided at the front and central position in the inner wall of the tray, said position being in the neighborhood facing a lingual frenum or a sublingual caruncle when said tray is inserted in the mouth. The through hole 35 improves the impression of the lingual frenum in the edentulous mouth.

The through hole 35 has the same shape, position and function as those of the through hole 15 in the improved mandibular stock tray for a dentulous mouth.

In the case of the edentulous mouth, if the tray is pressed strongly or loaded with a very small or large amount of impression material, a precise impression will not obtained or the mucous membrane will be injured by the tray. Thus, dentists should load the trays with an appropriate amount of impression material and keep them softly at no pressure for impression taking.

In FIGS. 16–20, reference numeral 36 indicates a small through hole provided at the front and central position in the outer wall of the tray, said position being in the neighborhood facing a mandibular median part when said tray is inserted in the mouth. The through hole 36 prevents the impression material from being separated from the tray when the tray is removed from the mouth after hardening of the material. As a result, the through hole 36 prevent the distortion of the form obtained by the impression taking.

The following advantages are obtained by the present invention.

(1) The impression of a mouth including important regions can be taken clearly and surely.

(2) The conventional process of taking an impression can be shortened. In prior art, a preliminary impression is taken with a stock tray to manufacture an individual tray, and then a precise impression is taken with the individual tray; in the present invention, the precise impression can be taken with the improved stock tray without an individual one, thereby shortening the process. As a consequence, the time required for treatment is shortened, so that burden imposed on both of a dentist and a patient is reduced.

(3) The elimination of the process of taking a preliminary impression and manufacturing an individual tray reduces the material and apparatus required for them, thereby achieving a significant cut in cost.

What is claimed is:

1. An improved maxillary dental stock tray for taking an impression of a dentulous mouth comprising:

a small through hole (3) at the front and central position in a side wall of the tray, said position in the tray inserted in a mouth being in the neighborhood facing an incisive papilla or a median frenum;

a projecting plate (4) at the convex and central position in a base of the tray, said position in the tray inserted in the mouth being in the neighborhood facing a median palatine raphe or a palatine foveola;

projections (5) at the rear edge positions in the base of the tray, said positions in the tray inserted in the mouth being in the neighborhood facing a hamular notch; and protuberances (6) at the rear end positions in an outer surface of the side wall of the tray, said positions in the tray inserted in the mouth being in the neighborhood facing a maxillary tuberosity.

2. The improved stock tray according to claim 1, wherein said plate (4) is disk-shaped, said projections (5) are sectorial and said protuberances (6) are semi-conical.

3. An improved mandibular dental stock tray for taking an impression of an edentulous mouth comprising:

projecting plates (13) at the rear end positions in an inner surface of an inner wall of the tray, said positions in the tray inserted in a mouth being in the neighborhood facing a mylohyoid muscle line;

projections (14) at the rear edge positions in a base of the tray, said positions in the tray inserted in the mouth being in the neighborhood facing a retromolar pad;

a small through hole (15) at the front and central position in the inner wall of the tray, said position in the tray inserted in the mouth being in the neighborhood facing a lingual frenum or a sublingual caruncle; and a small through hole (16) at the front and central position in an outer wall of the tray, said position in the tray inserted in the mouth being in the neighborhood facing lower front teeth or a median part.

4. The improved stock tray according to claim 3, wherein said plates (13) are disk-shaped and said projections (14) are sectorial.

5. An improved maxillary dental stock tray for taking an impression of an edentulous mouth comprising:

a small through hole (23) at the front and central position in a side wall of the tray, said position in the tray inserted in a mouth being in the neighborhood facing an incisive papilla or a median frenum;

a projecting plate (24) at the convex and central position in a base of the tray, said position in the tray inserted in the mouth being in the neighborhood facing a median palatine raphe or a palatine foveola;

projections (25) at the rear edge positions in the base of the tray, said positions in the tray inserted in the mouth being in the neighborhood facing a hamular notch; and protuberances (26) at the rear end positions in an outer surface of the side wall of the tray, said positions in the tray inserted in the mouth being in the neighborhood facing a maxillary tuberosity.

6. The improved stock tray according to claim 5, wherein said plate (24) is disk-shaped, said projections (25) are sectorial and said protuberances (26) are semi-conical.

7. An improved mandibular dental stock tray for taking an impression of an edentulous mouth comprising:

projecting plates (33) at the rear end positions in an inner surface of an inner wall of the tray, said positions in the tray inserted in a mouth being in the neighborhood facing a mylohyoid muscle line;

projections (34) at the rear edge positions in a base of the tray, said positions in the tray inserted in the mouth being in the neighborhood facing a retromolar pad;

a small through hole (35) at the front and central position in the inner wall of the tray, said position in the tray inserted in the mouth being in the neighborhood facing a lingual frenum or a sublingual caruncle; and a small through hole (36) at the front and central position in an outer wall of the tray, said position in the tray inserted in the mouth being in the neighborhood facing a mandibular median part.

8. The improved stock tray according to claim 7, wherein said plates (33) are disk-shaped and said projections (34) are sectorial.

* * * * *